(12) United States Patent
Bellinger et al.

(10) Patent No.: US 10,264,820 B2
(45) Date of Patent: *Apr. 23, 2019

(54) ELECTRONIC VAPORIZER THAT SIMULATES SMOKING WITH POWER CONTROL

(71) Applicant: Evolv, LLC, Ashtabula, OH (US)

(72) Inventors: John Bellinger, Cuyahoga Falls, OH (US); Brandon Ward, Ashtabula, OH (US)

(73) Assignee: EVOLV, LLC, Ashtabula, OH (US)

( * ) Notice: Subject to any disclaimer, the term of this patent is extended or adjusted under 35 U.S.C. 154(b) by 1135 days.

This patent is subject to a terminal disclaimer.

(21) Appl. No.: 14/338,512

(22) Filed: Jul. 23, 2014

(65) Prior Publication Data

US 2014/0332016 A1    Nov. 13, 2014

Related U.S. Application Data

(63) Continuation of application No. 13/661,184, filed on Oct. 26, 2012, now Pat. No. 8,820,330.

(Continued)

(51) Int. Cl.
*A24F 47/00* (2006.01)
*A61M 11/04* (2006.01)
(Continued)

(52) U.S. Cl.
CPC ......... *A24F 47/008* (2013.01); *A61M 11/041* (2013.01); *A61M 11/042* (2014.02); *A61M 15/06* (2013.01); *A61M 16/024* (2017.08); *A61M 16/161* (2014.02); *A61M 2016/0024* (2013.01); *A61M 2205/332* (2013.01);
(Continued)

(58) Field of Classification Search
CPC .. A24F 47/008; A61M 11/042; A61M 11/041; A61M 16/161; A61M 16/024; A61M 15/06; A61M 2016/0024; A61M 2205/3317; A61M 2205/3368;
(Continued)

(56) References Cited

U.S. PATENT DOCUMENTS

| 2,057,353 A | 10/1936 | Whittemore, Jr. |
| 3,934,117 A | 1/1976 | Schladitz |

(Continued)

FOREIGN PATENT DOCUMENTS

| CN | ZL200420031182.0 A2 | 8/2005 |
| EP | 0 358 114 A2 | 8/1989 |

(Continued)

OTHER PUBLICATIONS

International Search Report dated Mar. 7, 2016 for PCT/US2015/035154.

*Primary Examiner* — Shawntina Fuqua
(74) *Attorney, Agent, or Firm* — Kraguljac Law Group, LLC

(57) ABSTRACT

The claimed subject matter provides a control component that regulates output of an electronic vaporizer used to simulate smoking. The control component manages power to a heating element. A power detect component collects a parameter of the heating element to determine actual power output thereof. The control component dynamically adjusts the power source based on the actual power output.

18 Claims, 8 Drawing Sheets

Related U.S. Application Data

(60) Provisional application No. 61/553,129, filed on Oct. 28, 2011.

(51) Int. Cl.
*A61M 15/06* (2006.01)
*A61M 16/16* (2006.01)
*A61M 16/00* (2006.01)

(52) U.S. Cl.
CPC ............. *A61M 2205/3317* (2013.01); *A61M 2205/3368* (2013.01); *A61M 2205/3375* (2013.01); *A61M 2205/505* (2013.01); *A61M 2205/8206* (2013.01)

(58) Field of Classification Search
CPC .... A61M 2205/3375; A61M 2205/507; A61M 2205/8206; A61M 2205/332
See application file for complete search history.

(56) References Cited

U.S. PATENT DOCUMENTS

| | | | |
|---|---|---|---|
| 5,117,482 A | 5/1992 | Hauber | |
| 6,043,471 A * | 3/2000 | Wiseman | H05B 6/06 219/639 |
| 6,393,233 B1 | 5/2002 | Soulier | |
| 6,557,552 B1 | 5/2003 | Cox et al. | |
| 6,681,998 B2 | 1/2004 | Sharpe et al. | |
| 9,132,248 B2 | 9/2015 | Qiu | |
| 2004/0231667 A1* | 11/2004 | Horton | A61M 15/0065 128/202.13 |
| 2006/0081616 A1 | 4/2006 | Schuler | |
| 2010/0006565 A1 | 1/2010 | Ben-Shmuel et al. | |
| 2010/0212679 A1 | 8/2010 | Bishara | |
| 2011/0210105 A1 | 9/2011 | Romashko et al. | |
| 2011/0265806 A1* | 11/2011 | Alarcon | A24F 47/00 131/273 |
| 2012/0174914 A1* | 7/2012 | Pirshafiey | A61M 11/041 128/200.14 |
| 2012/0199663 A1 | 8/2012 | Qiu | |
| 2013/0032159 A1 | 2/2013 | Capuano | |
| 2014/0190477 A1 | 7/2014 | Qiu | |
| 2014/0190496 A1 | 7/2014 | Wensley et al. | |
| 2014/0338680 A1 | 11/2014 | Abramov et al. | |
| 2015/0059787 A1 | 3/2015 | Qiu | |
| 2015/0173124 A1 | 6/2015 | Qiu | |

FOREIGN PATENT DOCUMENTS

| | | |
|---|---|---|
| EP | 0 430 559 A2 | 6/1991 |
| EP | 0 703 735 B1 | 4/1996 |
| EP | 0 845 220 A1 | 6/1998 |
| EP | 1 618 803 A1 | 1/2006 |
| EP | 1 736 065 A1 | 12/2006 |
| EP | 2 022 349 B1 | 2/2009 |
| EP | 2 113 178 A1 | 11/2009 |
| EP | 2 327 318 A1 | 6/2011 |
| WO | 2007/131449 A1 | 11/2007 |
| WO | 2014/187770 A2 | 11/2014 |

\* cited by examiner

ELECTRONIC VAPORIZER THAT SIMULATES SMOKING WITH POWER CONTROL

CROSS-REFERENCE TO RELATED APPLICATIONS

This U.S. patent application is a continuation patent application of U.S. patent application Ser. No. 13/661,184 filed on Oct. 26, 2012, which claims the benefit of U.S. Provisional Application Ser. No. 61/553,129, filed Oct. 28, 2011, and entitled "POWER REGULATED ELECTRONIC CIGARETTE CONTROLLER." The entirety of the aforementioned applications are incorporated herein by reference.

SUMMARY

The subject innovation relates to a power regulated electronic vaporizer (or a component and/or circuitry thereof) for a smoking simulator device in which direct regulation of the input or output power provides a uniform and consistent user experience. The electronic vaporizer includes a heating element, a power source that provides power to the heating element, and a trigger component that activates the heating element to vaporize a material from a cartridge for consumption (e.g., inhale, smoke, and the like). The electronic vaporizer further includes a control component that is configured to adjust the power source to regulate a vaporization of the material from the cartridge for a uniform distribution to the user, wherein the adjustment is based upon a power output or a power input from a component to the heating element.

In an embodiment, a controller component for an electronic vaporizer is provided. The controller component for an electronic vaporizer device can be used to simulate smoking. The controller component includes a first component configured to determine an actual measured power output to a heating element. The controller component includes a second component configured to control a power source that powers the heating element based on the actual measured power output.

In an embodiment, a controller component for an electronic vaporizer is provided. The controller component for an electronic vaporizer device can be used to simulate smoking. The controller component includes a first component configured to determine an actual measured power input to a heating element. The controller component includes a second component configured to control a power source that powers the heating element based on the actual measured power input.

In an embodiment, a method is provided. The method can control an electronic vaporizer in a simulated smoking device. The method includes selecting a power output value, measuring an actual power value for a heating element of the electronic vaporizer, calculating an output based on the power output value and the actual power value, and utilizing the output to drive a power value for the heating element of the electronic vaporizer.

The following description and the annexed drawings set forth in detail certain illustrative aspects of the claimed subject matter. These aspects are indicative, however, of but a few of the various ways in which the principles of the innovation may be employed and the claimed subject matter is intended to include all such aspects and their equivalents. Other advantages and novel features of the claimed subject matter will become apparent from the following detailed description of the innovation when considered in conjunction with the drawings.

DETAILED DESCRIPTION

Figure 1:
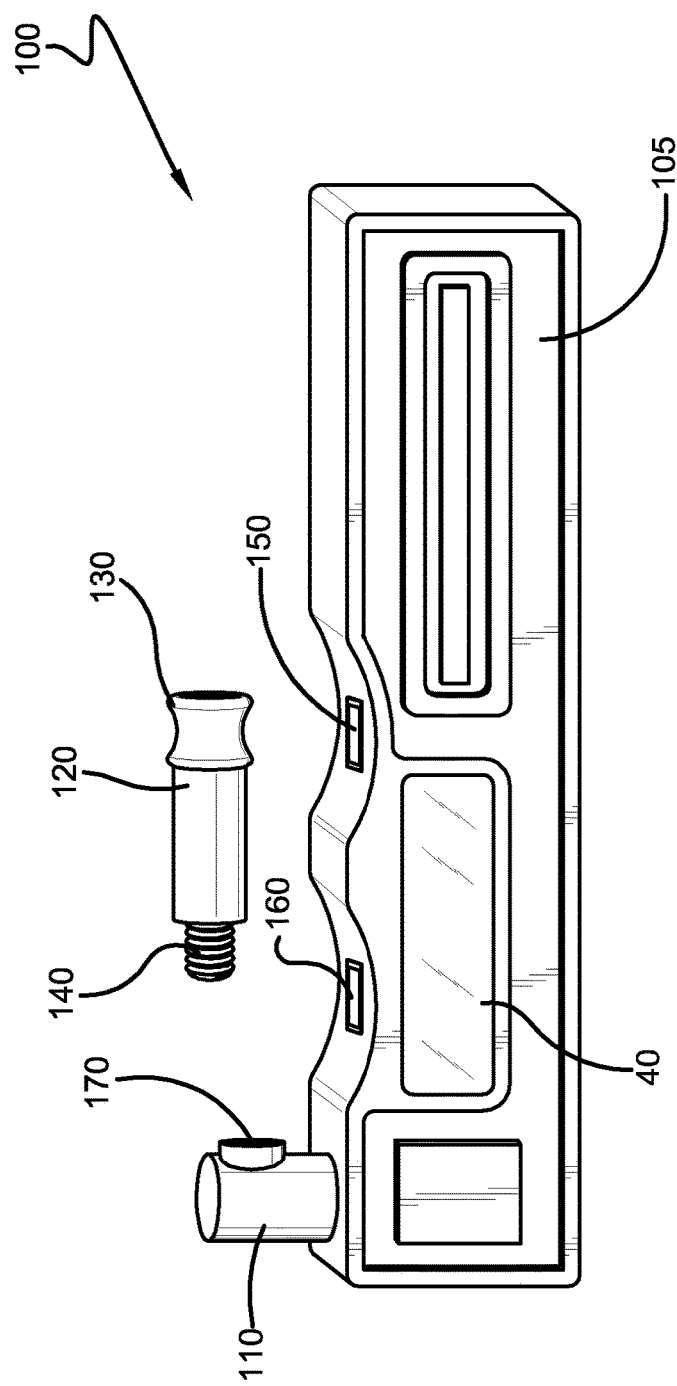
FIG. 1 illustrates a perspective view of an electronic vaporizer that simulates smoking.

The subject innovation pertains generally to a control component that regulates output of an electronic vaporizer that simulates smoking or inhaling of a material. The control component manages a power output to a heating element. In an embodiment, a power detect component collects a parameter related to the heating element to determine actual power output thereof. Based on a selected power output level and the aggregated parameter(s), the control component dynamically adjusts the a power output or a power input of the power source.

The claimed subject matter is described with reference to the drawings, wherein like reference numerals are used to refer to like elements throughout. In the following description, for purposes of explanation, numerous specific details are set forth to provide a thorough understanding of the subject innovation. It may be evident, however, that the claimed subject matter may be practiced without these specific details. In other instances, well-known structures and devices are shown in block diagram form to facilitate describing the subject innovation.

Features that are described and/or illustrated with respect to one embodiment may be used in the same way or in a similar way in one or more other embodiments and/or in combination with or instead of the features of the other embodiments. These and further aspects and features will be apparent with reference to the following description and attached drawings. In the description and drawings, particular embodiments of the subject innovation have been disclosed in detail as being indicative of some of the ways in which the principles of the subject innovation may be employed, but it is understood that the subject innovation is not limited correspondingly in scope. Rather, the subject innovation includes all changes, modifications and equivalents coming within the scope of the claims appended hereto. The accompanying illustrations are examples of the subject disclosure, but the innovation can appear in various embodiments depending on varying sleeve lengths and personal customizations that are not illustrated here.

Of course, those skilled in the art will recognize many modifications may be made to this configuration without departing from the scope or spirit of the claimed subject matter. Moreover, the word "exemplary" is used herein to mean serving as an example, instance, or illustration. Any aspect or design described herein as "exemplary" is not necessarily to be construed as preferred or advantageous over other aspects or designs. It should be emphasized that the term "comprises/comprising" when used in this specification is taken to specify the presence of stated features, integers, steps or components but does not preclude the presence or addition of one or more other features, integers, steps, components or groups thereof.

FIG. 1 illustrates an electronic vaporizer 100 that simulates smoking or inhaling of a material that is vaporized. The electronic vaporizer 100 includes a casing 105 that houses components such as, but not limited to a power source (discussed in more detail below). The electronic vaporizer 100 further includes a connective port 110 that is operative to receive a cartridge 120 which contains a material for vaporization and inhaling, wherein the cartridge 120 can include a mouth piece 130 on one end and a connector 140 on an opposite end. A heating element (discussed in more detail below) can be included or incorporated in the cartridge 120. It is to be appreciated and understood that the cartridge 120 includes a heating element which can be controlled by one or more components included within the electronic vaporizer 100. Thus, although the cartridge 120 and heating element can be a separate component or element of the electronic vaporizer 100, control of the heating element can be based on components included within the electronic vaporizer 100. The cartridge 120 can physically connect to the electronic vaporizer 100 via the connective port 110 and the connector 140. For instance, the connector 140 and the connective port 110 can be a male/female connection, a threaded connection, among others. It is to be appreciated that any suitable connective means can couple the cartridge 120 to the electronic vaporizer 100. In an embodiment, the connective port 110 can be used as an on/off switch to power on or power off the electronic vaporizer 100. By way of example and not limitation, the connective port 110 can be twisted in a first direction (e.g., clockwise) to turn on the electronic vaporizer 100 and twisted in a second direction (e.g., counter-clockwise) to turn off the electronic vaporizer 100. In another embodiment, the electronic vaporizer 100 can include a designated on/off switch (not shown) that can power on or power off the electronic vaporizer 100.

The electronic vaporizer 100 can further include a display 40 that displays or renders information, data, and the like. For instance, the display 40 can communicate information such as, a letter, a number, a symbol, a picture, a graphic, a reading, a measurement, a current, a voltage, a power output, a resistance, among others. The display 40 can be, for instance, an LED display, a backlit display, an LCD display, a plasma display, among others. In an embodiment, the display 40 can be a touchscreen that provides data as well as receives an input. A first input 150 can further be included with the electronic vaporizer 100 in which the first input 150 initiates an output for user consumption (e.g., inhaling, smoking, and the like). For example, the first input 150 can light up the display 40 and/or activate a vaporization of the material in the cartridge 120 for consumption. A second input 150 can be also included with the electronic vaporizer 100, wherein the second input 150 can be for user input (e.g., dial, potentiometer, setting control, display 40 brightness, among others).

The electronic vaporizer 100 simulates the act of smoking by producing an inhaled vapor bearing the physical sensation, appearance, and often the flavor (e.g., with or without nicotine content) of inhaled smoke. For instance, the electronic vaporizer 100 can simulate the act of smoking tobacco, flavored tobacco, Mu'assel, Sheesha, medicinal marijuana, among others. It is to be appreciated that the material that is smoked is not to be limiting on the subject innovation and that the electronic vaporizer 100 can be used with a suitable material that allows the simulation of smoking or inhaling vapors from such material. The electronic vaporizer 100 simulates smoking without the ill effects such as odor, health risks, among others since vapor is inhaled or consumed rather than actual smoke from the material.

The electronic vaporizer 100 can use heat to vaporize a material into a mist for inhalation or consumption. The material can be contained within the cartridge 120, wherein the material can be, but is not limited to being, propylene glycol, glycerin-based liquid solution, among others. The electronic vaporizer 100 can be a portable electronic hand-held device that vaporizes a material for inhaling by a user in which the inhaling and consumption simulates the act of smoking.

The electronic vaporizer 100 can be portable, self-contained device that can vary in size, shape, colors, and the like. In an embodiment, the electronic vaporizer 100 can be a cylindrical-based or rectangular-based shaped device. Yet, any shape, size, dimensions, or material may be chosen with sound engineering judgment without departing from the intended scope of coverage of the embodiments of the subject invention. In an embodiment, the electronic vaporizer 100 can be a reusable device with replaceable or refillable components. In another embodiment, the electronic vaporizer 100 can be disposable or with disposable components.

It is to be appreciated that the subject innovation is not to be limited to the material used or vaporized with the electronic vaporizer 100 for personal inhaling or consumption. For instance, the material can be a liquid with various flavors, nicotine, nicotine-free, various nicotine concentrations, among others. Moreover, the material can be a marijuana-based material that can be vaporized for inhalation in relation to medicinal purposes, for instance.

As discussed above, an electronic vaporizer (also referred to as an electronic cigarette) can be a device consisting of a battery (e.g., a power source) and a heating element which is used to vaporize a flavored, sometimes nicotine-containing fluid, plus a casing and user interface. Conventional electronic cigarettes contain charging circuitry for the power source or voltage adjustments to change the feel and quantity of vapor inhaled by the user. The following is an overview of conventional techniques utilized with electronic cigarettes.

Conventional heating elements used in electronic cigarettes do not have stable resistances. Heating elements are considered a consumable part in an electronic cigarette. The resistance changes with temperature, so as the electronic cigarette is used repeatedly in a short period of time, the resistance will not be the same between the first output from the electronic cigarette and a later output from the electronic cigarette. Further, the fluids or materials being vaporized tend to leave a residue on the heating element. This residue is conductive, so as the residue builds up, the overall resistance of the heating element changes (e.g., the resistance of the heating element varies over time). Conventional electronic cigarettes are powered by batteries, usually lithium ion type. Lithium ion batteries can have a fully charged voltage of 4.2 volts, and a fully discharged voltage of 3.0 volts.

Conventional control circuitry can include a direct battery voltage. Conventional electronic cigarettes (e.g., also referred to as e-cigarette) connect a heating element to a power source directly through a switch or a trigger component. This causes the voltage of a heating element to vary, for instance, between 4.2 volts and 3.0 volts for a typical e-cigarette with a power source (e.g., a lithium battery). For example, a resistive heater element can vary between 3 ohms resistance and 2 ohms resistance, depending on factors such as, but not limited to, age, temperature, material being vaporized, and manufacturing variation (e.g., material of construction, composition of materials, inconsistencies in connections, among others). This can cause a power level in a heating element for a directly connected power source to vary, for instance, between 3 watts and 9 watts, without user control resulting in a highly inconsistent user experience (e.g., varying output, inconsistent vaporization, among others).

Conventional control circuitry can regulate voltage. Conventional electronic cigarettes use a controlled output voltage, generated with commodity switching or linear voltage regulators, to supply a constant voltage to a heating element. For instance, conventional voltage controlled electronic cigarettes are either adjustable between, for instance, 4 volts and 6 volts, or fixed at some output voltage such as, for instance, 5 volts. Conventional voltage controlled electronic cigarettes provide a tolerable user experience because a voltage is regulated for the output. For instance, a typical 5 volt voltage regulated electronic cigarette can have an output power somewhere between 12.5 watts if a heating element has a resistance of 2 ohms, to 8.3 watts if a heater element has a resistance of 3 ohms. This range of 12.5 watts to 8.3 watts impacts the vapor output of the device.

The subject innovation overcomes the above stated deficiencies by providing an improved electronic control method for regulating power delivered to a heating element used by the electronic vaporizer 100, thereby controlling the quantity and quality of vapor produced by the electronic vaporizer 100. An improved electronic vaporizer power control system can directly control the output power generated in a heating element, regardless of a resistance of a heating element or state of a power supply. This control results in a much more consistent user experience and uniform output.

Figure 2:
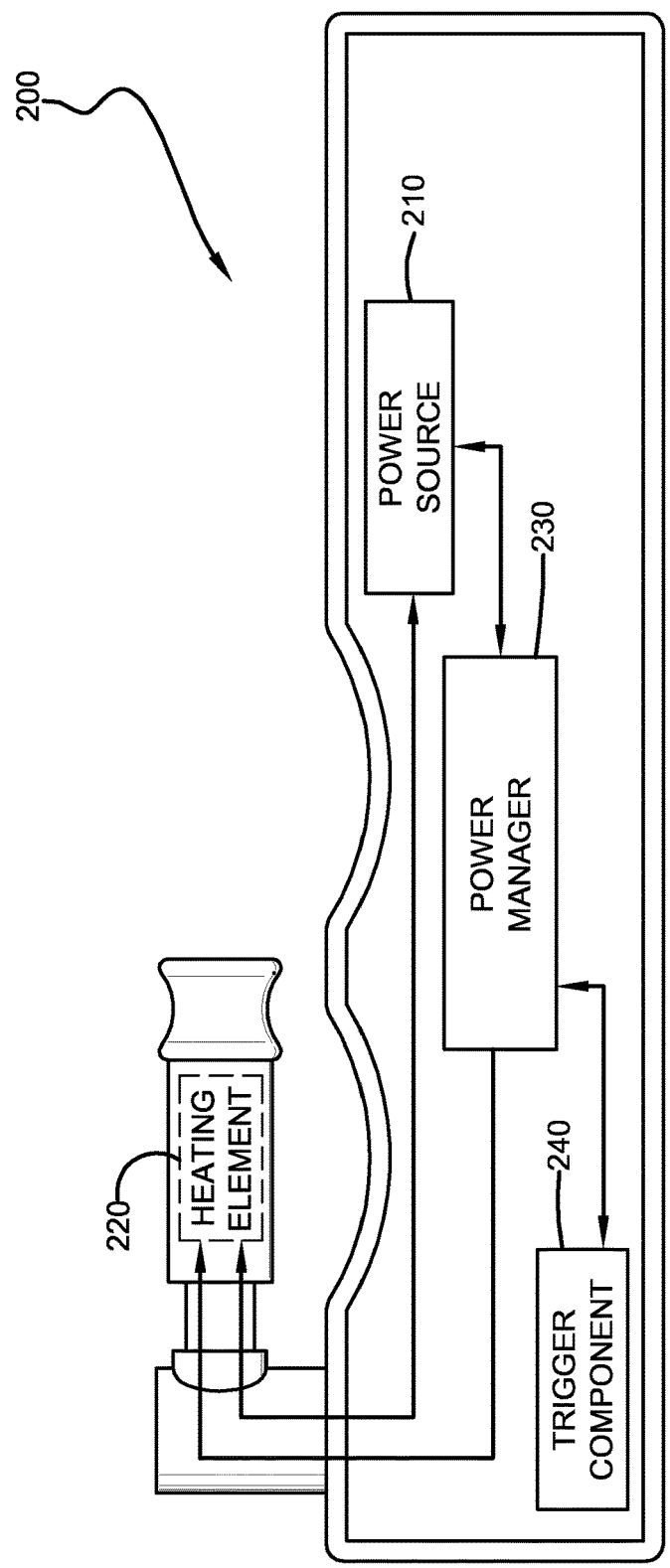
FIG. 2 illustrates a system that manages output for an electronic vaporizer.

FIG. 2 illustrates a system 200 that manages output for the electronic vaporizer 100. The electronic vaporizer 100 includes components that provide vaporization of a material for consumption for a user. The electronic vaporizer 100 includes a power source 210 that provides power to a heating element 220, wherein the heating element 220 generates heat to vaporize a material for a user to inhale or consume. As discussed, although the heating element 220 is within the cartridge (discussed in FIG. 1), control can be included within the electronic vaporizer 100. It is to be appreciated and understood that the power source 210 can be a battery, a Lithium Ion battery, a Universal Serial Bus (USB) power source, or a suitable power source that powers the heating element 220. The electronic vaporizer 100 further includes a trigger component 240 that activates the heating element 220 to vaporize a material for user consumption. By way of example and not limitation, the trigger component 240 can be an input such as a button, a dial, a touch screen, a proximity sensor, a voice detection, a motion sensor, a switch, a suction sensor, a pressure sensor, a pressure switch, or a combination thereof.

The electronic vaporizer 100 further includes a power manager 230 that controls a power output or power input to the heating element 220 via adjustment to the power source 210, wherein the adjustment is based on a measured parameter associated with the heating element 220. In an embodiment, the power manager 230 can control power to the heating element 220 based on an actual measured power output of the power source 210. In such embodiment, the power manager 230 can adjust a current from the power source 210 to generate a selected power output. In another example, the power manager 230 can adjust a voltage from the power source 210 to generate a selected power output. In such embodiment, the power manager 230 can adjust the power source 210 directly to generate a selected power output. In such embodiment, the power manager 230 can adjust the power source 210 directly utilizing an average power calculation.

In another embodiment, the power manager 230 can control power to the heating element 220 based on an actual measured power input of the power source 210. In such embodiment, the power manager 230 can adjust a current from the power source 210 to generate a selected power output. In such embodiment, the power manager 230 can adjust a voltage from the power source 210 to generate a selected power output. In such embodiment, the power manager 230 can adjust the power source 210 directly to generate a selected power output. In such embodiment, the power manager 230 can adjust the power source 210 directly utilizing an average power calculation In another embodiment, the power manager 230 can adjust a duty cycle for the power source 210 to control the power output or power input to the heating element 220. The power manager 230 can measure an actual power output for the heating element 220 based on, for instance, a current of the heating element 220, a resistance of the heating element 220, a voltage of the heating element 220, average power input, average power output, power based on efficiency of a portion of circuitry or component, and/or any suitable manner in which power is calculated with one or more components. A selected power output can be identified, wherein the selected power output can be a variable value defined by the user, a predefined value, a set value, a calculation from a controller component of the electronic vaporizer, or a combination thereof. The power manager 230 can adjust power to the heating element 220 based on the actual power output (e.g., measured power output) and/or the selected power output. In other words, if the actual power output of the heating element 220 differs from the selected power output, the power output of the power source 210 can be adjusted.

Inside heating element 220, the heat supplied performs three functions. First, the heat raises a temperature of the fluid (e.g., material to be vaporized for inhalation) to a boiling point. Second, the heat boils some of the fluid or material. Third, the heat heats a resulting vapor above the boiling point (e.g., boiling temperature). Because the heat of vaporization can be larger than the liquid specific heat of the fluid or material, additional heat transfer into the vapor is limited by a higher thermal resistance of the heater-vapor interface. Additionally, the vapor is being drawn away from the heating element 220 by suction created by the user, resulting in a majority of the heat generated in the heating element going to vaporizing the fluid or material. Therefore, by controlling the power input (e.g., in watts) to the heating element 220, a quantity of vapor produced can be controlled.

Controlling the output based on power creates a uniform, consistent user experience based on the regulated output even as the heating element 220 or the power source 210 changes, degrades, among others.

The power manager 230 can measure or collect measurements of two of the following: a heating element resistance, an output voltage to the heating element 220, and an output current of the heating element. From these, an actual power output of the heating element 220 can be calculated or measured by use of Ohm's law (e.g., Voltage=Current*Resistance, or a variation thereof) and a definition of power output (e.g., Power=Voltage*Current, or a variation thereof). The power manager 230 can directly control power to produce a regulated and uniform output from the vaporization of the material from the heating element. In an embodiment, a control loop can be used (e.g., feedback, feedforward, among others) to dynamically control the power output to the heating element 220.

Figure 6:
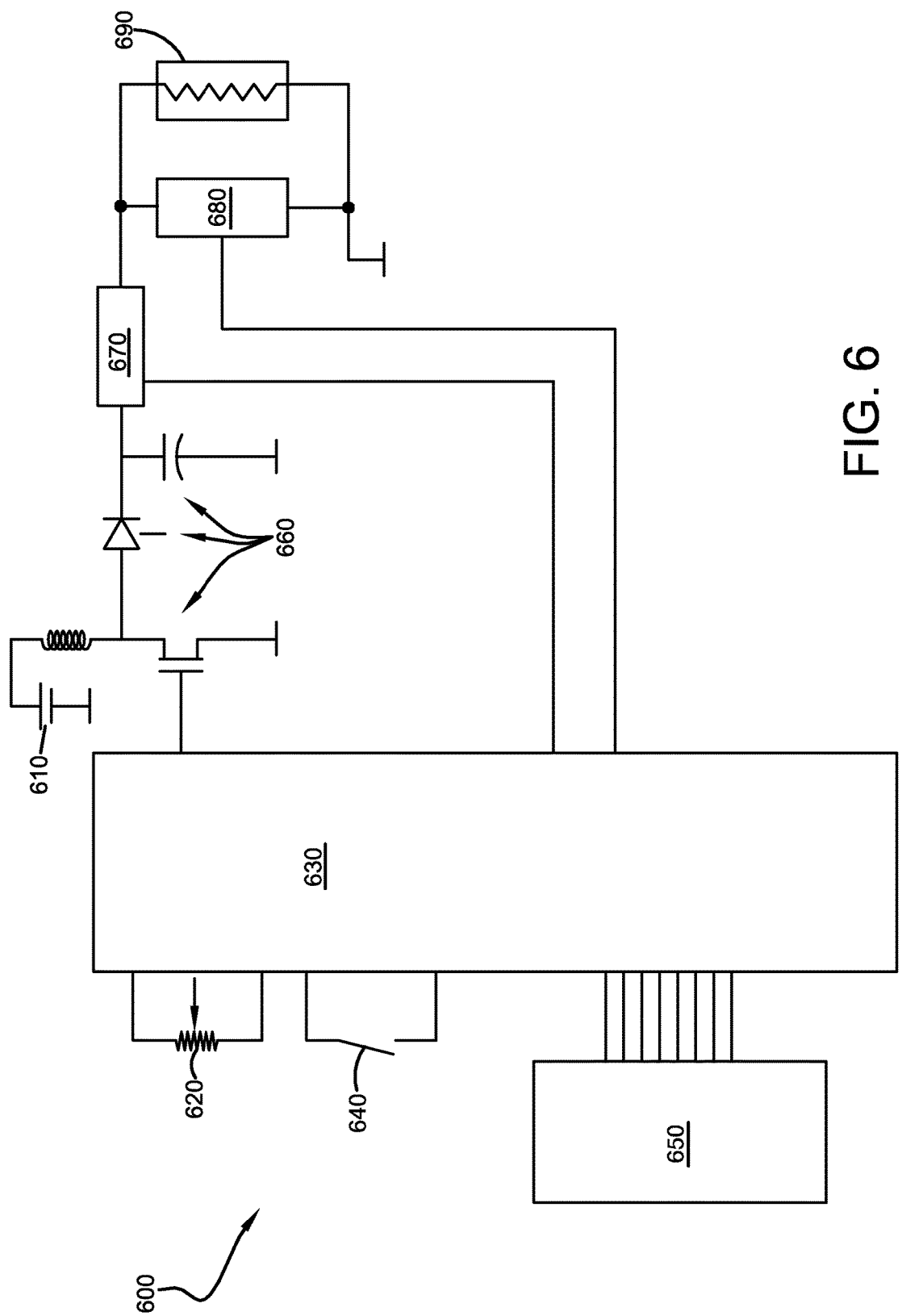
FIG. 6 illustrates a circuit diagram for power regulation in an electronic vaporizer.
Figure 7:
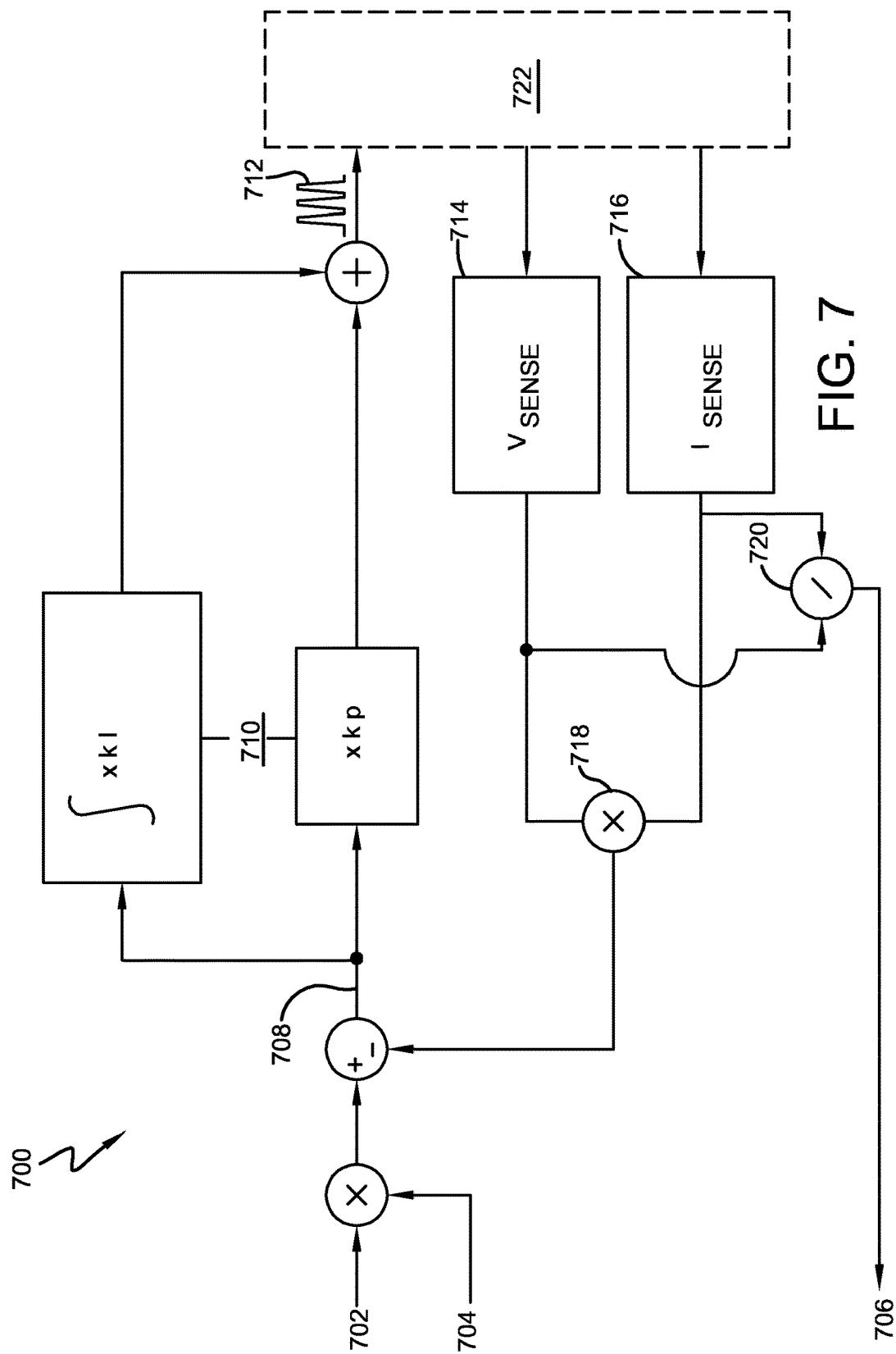
FIG. 7 illustrates a control loop diagram 700 implementing power regulation for an electronic vaporizer.

In an embodiment, a direct power regulator can be utilized in which the direct power regulator uses a microcontroller to measure a system property or parameter, perform control in software, and then output a control signal to a standard DC-DC structure, such as a regulator (e.g., boost regulator, among others). It is to be appreciated that any suitable combination of hardware, software, or circuitry can be implemented with the subject innovation and the disclosed examples are not to be limiting. For example, FIGS. 6 and 7 illustrate circuit diagrams for implementation of the subject innovation (discussed in more detail below). In an embodiment, the power manager 230 can adjust a current from the power source 210 to generate a selected power output. In an embodiment, the power manager 230 can adjust a voltage from the power source 210 to generate a selected power output.

Figure 3:
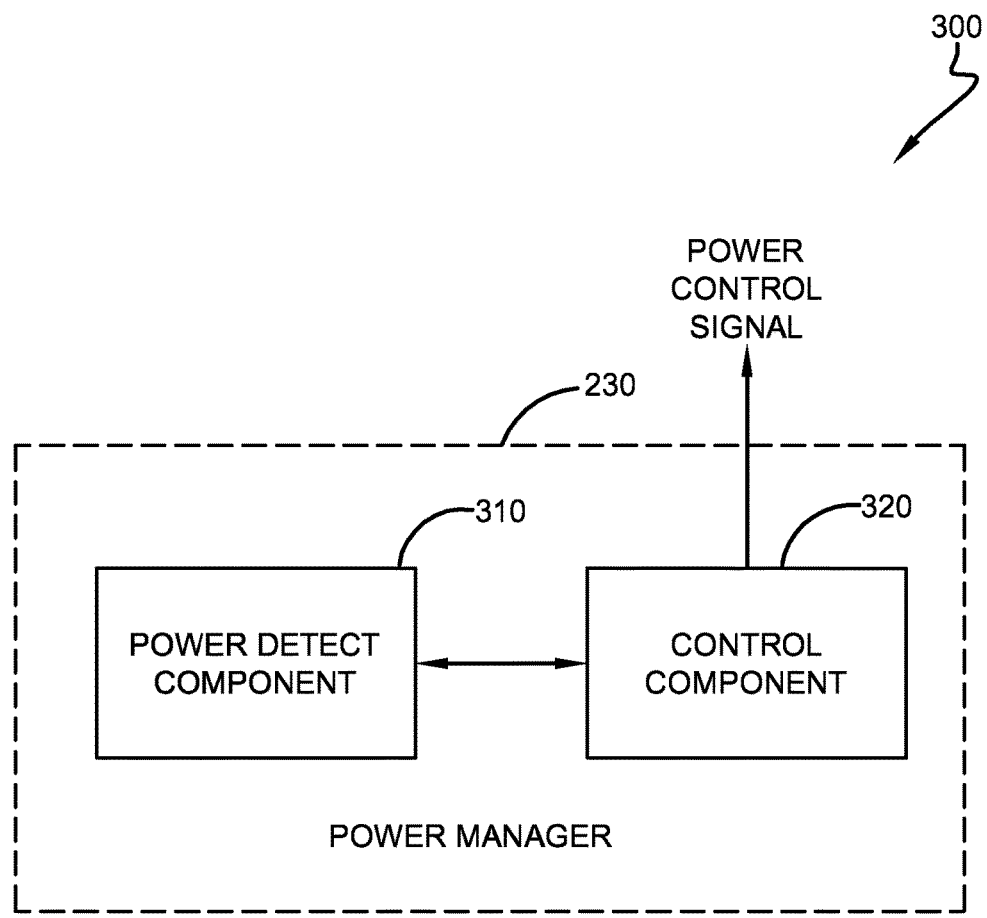
FIG. 3 illustrates a system that regulates an output for an electronic vaporizer based on an actual power output and a selected power output.

It is to be appreciated and understood that power manager 230 can be a single component (as depicted) or parsed into sub-components (see FIG. 3 for example). Power manager 230 is illustrated as a stand-alone component solely as an example and is not to be limiting on the subject innovation. For instance, power manager 230 can be a stand-alone component (as depicted), incorporated into the power source 210, incorporated into the trigger component 240, incorporated into the heating element 220, integrated into legacy control system, coupled to a legacy control system, or a suitable combination thereof.

FIG. 3 illustrates a system 300 that regulates an output for an electronic vaporizer based on an actual power output and a selected power output. The system 300 can be a power regulator system in which the power manager 230 includes a power detect component 310 and a control component 320. The power detect component 310 is configured to measure at least one parameter associated with the heating element (illustrated in FIG. 2) in which the at least one parameter is used to measure actual power output of the heating element. By way of example and not limitation, the parameter can be a voltage of a heating element (e.g., received via the power source), a current of the heating element, a resistance of the heating element, a power output to the heating element, a power input to the heating element, an average power, a power efficiency of a portion of circuitry or component used by the electronic vaporizer, instantaneous output power, average input power, instantaneous input power, among others.

The system 300 can further include a safety check based upon measured parameters (e.g., voltage, power, current, a power input to the heating element, an average power, a power efficiency of a portion of circuitry or component used by the electronic vaporizer, instantaneous output power, average input power, instantaneous input power, among others) of the electronic vaporizer and/or a component thereof. For instance, based on the detected parameters of the electronic vaporizer (via the power detect component 310, for instance), the system 300 can be managed (e.g., shut down, error message displayed, time delay for use/activation, among others) in order to ensure safety of at least one of a user, a component/element of the electronic vaporizer, the electronic vaporizer, or a combination thereof.

The control component 320 is configured to generate a control signal to the power source (shown in FIG. 2) in order to adjust or manage the actual power output (e.g., measured power output). For instance, a power output can be adjusted, a power input can be adjusted, a voltage can be adjusted, a current can be adjusted, an average power can be adjusted, among others.

The control component 320 (e.g., also referred to as a regulator module) can output a controlled power level to the heater element, regardless of changes to the input voltage or output resistance. The control component 320 can measure output or input voltage and current, multiply these in software, hardware, or a combination thereof. The control component 320 uses the result of the multiplication as a resulting power signal and provides such signal as an input to a control loop in a converter (e.g., DC/DC converter for instance). The control loop can be implemented in software, hardware, analog hardware, or a combination thereof.

The control component 320 can use 1) a measure or calculation of an input power of the heating element or 2) a combination of an input voltage, an output voltage, a current, a resistance, and 3) a calculation or approximation of a converter efficiency to regulate output power. The control component 320 can further utilize a feedback or feedfoward that is a portion of software, a portion of hardware, a portion of analog hardware, or a combination thereof. For instance, a feedback, feedforward, or control loop could employ a sample rate between a range of 1 Hz to 2,500 Hz. In another embodiment, a sample rate of 2,000 Hz could be employed. In another embodiment, a continuous analog system can be employed. Still, a sample rate can be employed with sound engineering judgment without departing from the intended scope of coverage of the embodiments of the subject invention.

The control component 320 can dynamically update a display of the electronic vaporizer, wherein the display renders the output power provided to the heating element. The control component 320 can calculate and/or display the resistance of the output heating element (e.g., display to user). The control component 320 can include an input that allows the user to adjust the regulated output power level directly, wherein the input is at least one of a potentiometer, pushbutton, a voice command, or a user interface. The control component 320 can further be fixed to a specific output power.

Figure 4:
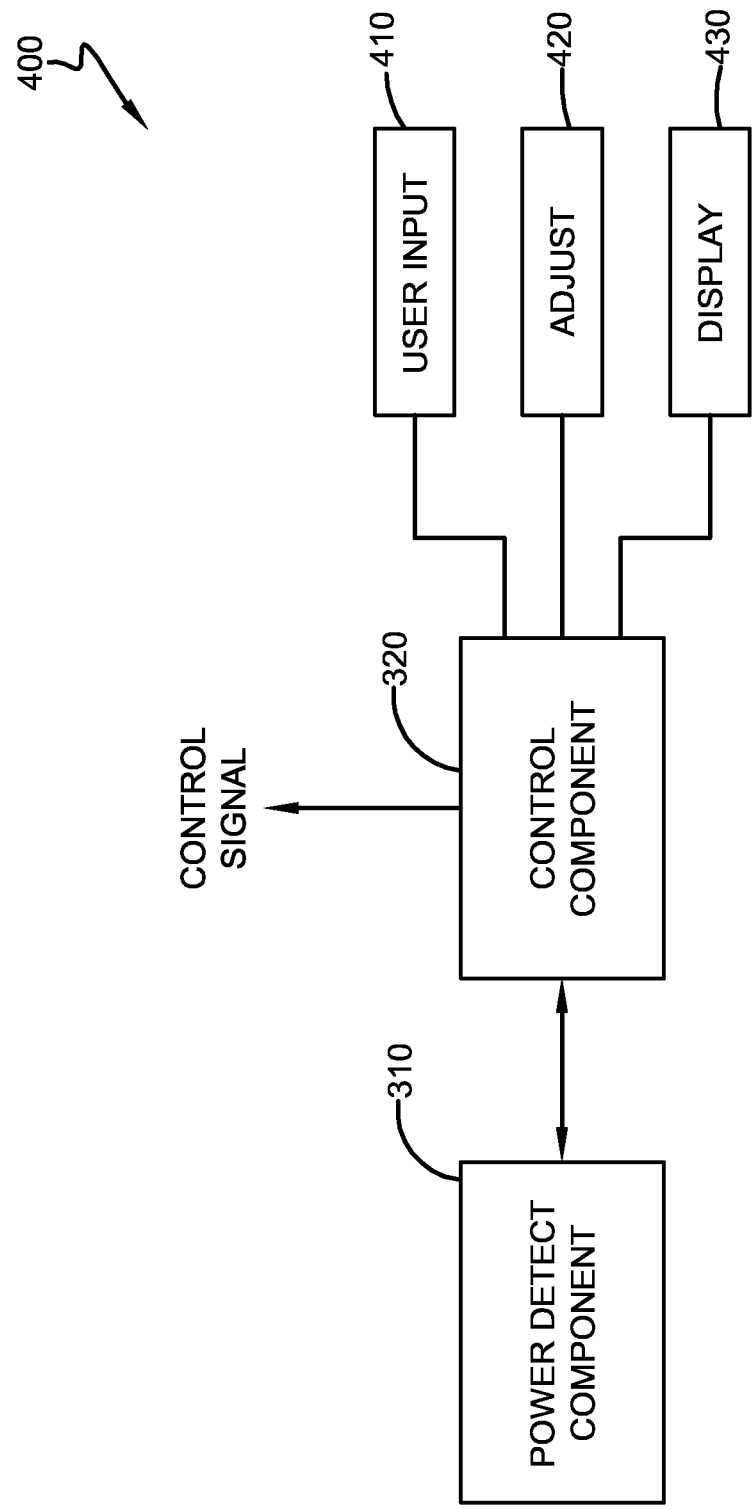
FIG. 4 illustrates a system that provides uniform control of a heating element of an electronic vaporizer based on dynamic measurements related to power consumption of the heating element.

FIG. 4 illustrates a system 400 that provides uniform control of a heating element of an electronic vaporizer based on dynamic measurements related to power output to the heating element. The system 400 includes the power detect component 310 that is configured to detect actual measured power input or output. The power detect component 310 is further configured to calculate an actual power output to the heating element. Furthermore, the system 400 includes the control component 310 that is configured to regulate a power output from a power source (based upon the power detect component 310) to regulate an output from the electronic vaporizer.

The system 400 further includes a user input 410. The user input 410 can be a selected power output in which the control component 320 adjusts the power output of the power source to target the selected power output. The user input 410 can be an input related to, but not limited to, a setting, a resistance level, a power level, an activation of the heating element, a trigger for generation of output for inhaling, a security mechanism (e.g., a password, a thumbprint, a unique indicia, a voice command, a pattern, among others), among others. The user input 410 can be a suitable input such as, but not limited to, a button (press activated), a touch activated button, a touch screen, a proximity detector, a moisture sensor, a temperature sensor, a suction sensor, a pressure switch, a pressure sensor, among others.

An adjust component 420 can be utilized with the control component 320 to manually change a setting related to the electronic vaporizer. By way of example and not limitation, the setting can be a selected power output for the power source, type of material for vaporization and consumption, and the like.

The system 400 can further include a display 430. The term display collectively refers to any component capable of providing information to a user including audio, visual or tactile methods of conveying information. In the example shown, a visual display is used. A suitable visual display is one that can render a portion of a graphic, a letter, a number, a symbol, a color, among others. The visual display can be an LED screen, a dot matrix screen, a Liquid Crystal Display (LCD) screen, a plasma screen, a touch screen, a display with a flexible property, among others. The display 430 can convey information in real time. For instance, the display 430 can provide operating condition information to the user including current (e.g., current of heating element, current of power source, and the like), voltage (e.g., voltage of the heating element, voltage of the power source, and the like), resistance (e.g., resistance of the heating element, and the like), a power output (e.g., a selected power output, a defined or fixed power output, a power output of the power source, a power output to the heating element, and the like), or a combination thereof.

Figure 5:
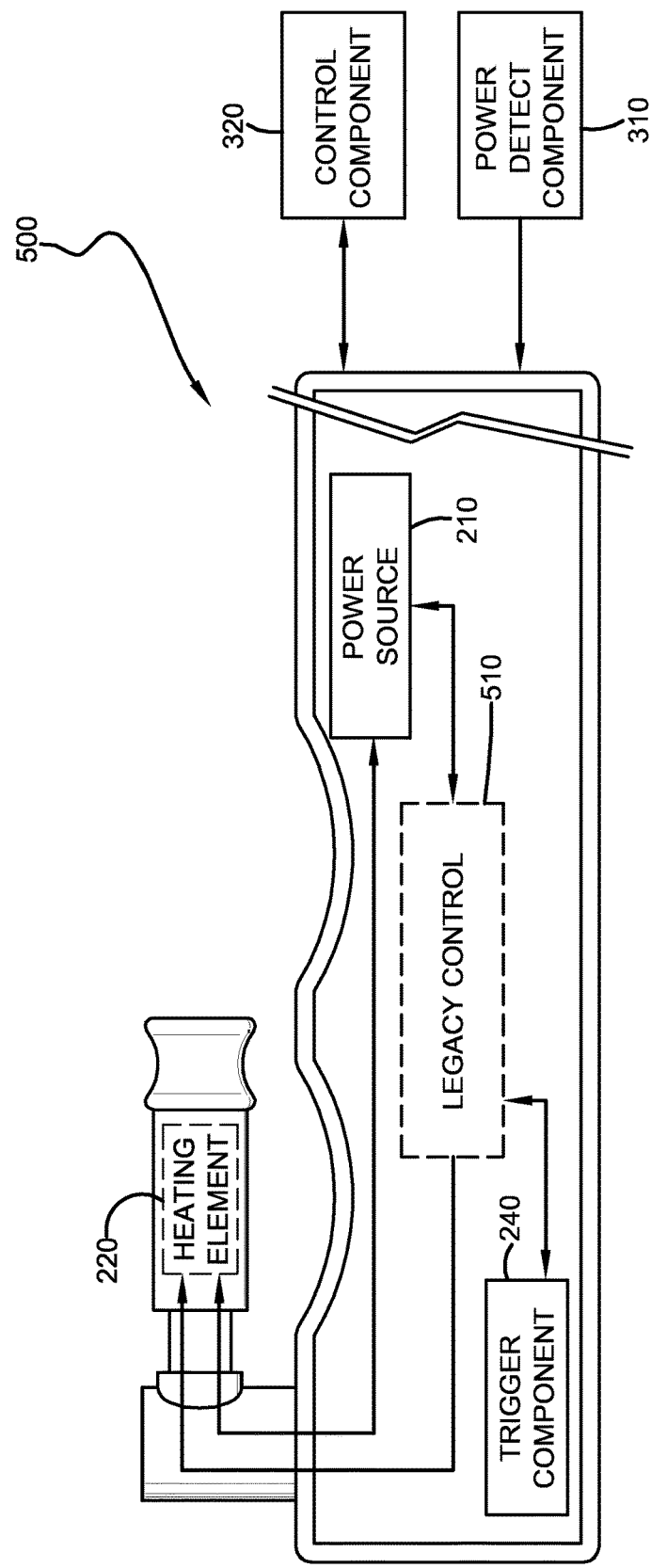
FIG. 5 illustrates an electronic vaporizer that simulates smoking with variable voltage control and a coupled power management system.

FIG. 5 illustrates an electronic vaporizer 500 for simulating smoking with a control system that uniformly regulates the heating element. The electronic vaporizer 500 includes the power source 210, the heating element 220, the trigger component 240. It is to be appreciated that the heating element 220 can be included within a cartridge. Yet, the control system can be included within the electronic vaporizer 500 or a component included or used therewith. For example, the control system can be included within any suitable component or part of the electronic vaporizer. The electronic vaporizer 500 may or may not include a legacy control component 510. For instance, the electronic vaporizer 500 can include the legacy control component 510. In another example, the electronic vaporizer 500 does not include a control system or control circuitry. The legacy control component 510 is a conventional control module for the electronic vaporizer 500.

The control component 320 and/or the power detect component 310 can be utilized with the electronic vaporizer 500 to include power output control to the legacy control component 510. In an embodiment, the control component 320 and/or the power detect component 310 can be retrofitted to the legacy control component 510 to provide enhanced control of output of an electronic vaporizer. In another embodiment, the control component 320 and/or the power detect component 310 can leverage at least one of the elements or components utilized in the electronic vaporizer. For instance, the control component 320 and/or the power detect component 310 can utilize at least one of the power source 210, the heating element 220, or the trigger component 240. Such retro-fitting enables the legacy control component 510 to be enhanced to manage output of the electronic vaporizer in a uniform manner based on power output to the heating element 220. For example, the control component 320 and/or the power detect component 310 can be incorporated into the electronic vaporizer 500, physically coupled to the electronic vaporizer 500, physically attached to the electronic vaporizer 500, electronically coupled to at least one of the power source 210, the heating element 220, the legacy control component 510, the trigger component 640, or a suitable combination thereof.

FIG. 6 illustrates a circuit diagram 600 for power regulation in an electronic vaporizer. The circuit diagram 600 can include a power source 610, a potentiometer for user adjustment (e.g., adjustment of a selected power output), a microcontroller 630, a switch 640 (e.g., switch for user activation of the electronic vaporizer), a display 650, a converter 660 (e.g., a boost converter, and the like), an output current sensor 670, an output voltage sensor 680, and a heating element 690. It is to be appreciated that the circuit diagram 600 is solely for exemplary purposes only and that any suitable variation can be implemented in hardware, software, or a combination thereof.

FIG. 7 illustrates a control loop diagram 700 implementing power regulation for an electronic vaporizer. The circuit diagram 700 can include a power control input signal 702, an on/off control input signal 704, a measured resistance to output to display 706, an error term for a control loop 708, a control loop 710 (e.g., a proportional integral type control loop, a feed forward control loop, among others), an output Pulse-Width Modulation (PWM) signal to regulator 712, a voltage sense with scaling and conditioning 714, a current sense with scaling and conditioning 716, a calculated measured power signal 718, a calculated measured resistance signal 720, and a converter 722 (e.g., a hardware boost converter, an external to software hardware boost regulator, or the like). It is to be appreciated that the circuit diagram 700 is solely for exemplary purposes only and that any suitable variation can be implemented in hardware, software, or a combination thereof.

The aforementioned systems, components (e.g., power manager, control component, power detect component, etc.), and the like have been described with respect to interaction between several components and/or elements. It should be appreciated that such devices and elements can include those elements or sub-elements specified therein, some of the specified elements or sub-elements, and/or additional elements. Further yet, one or more elements and/or sub-elements may be combined into a single component to provide aggregate functionality. The elements may also interact with one or more other elements not specifically described herein for the sake of brevity, but known by those of skill in the art.

Furthermore, as will be appreciated, various portions of the disclosed systems above and methods below can include or consist of artificial intelligence, machine learning, or knowledge or rule-based components, sub-components, processes, means, methodologies, or mechanisms (e.g., support vector machines, neural networks, expert systems, Bayesian belief networks, fuzzy logic, data fusion engines, classifiers, among others). Such components, inter alia, can automate certain mechanisms or processes performed thereby to make portions of the systems and methods more adaptive as well as efficient and intelligent. By way of example and not limitation, the power manager 230 or one or more subcomponents thereof can employ such mechanisms to efficiently determine a power output to approximate to an actual power of a heating element associated with an electronic vaporizer.

Figure 8:
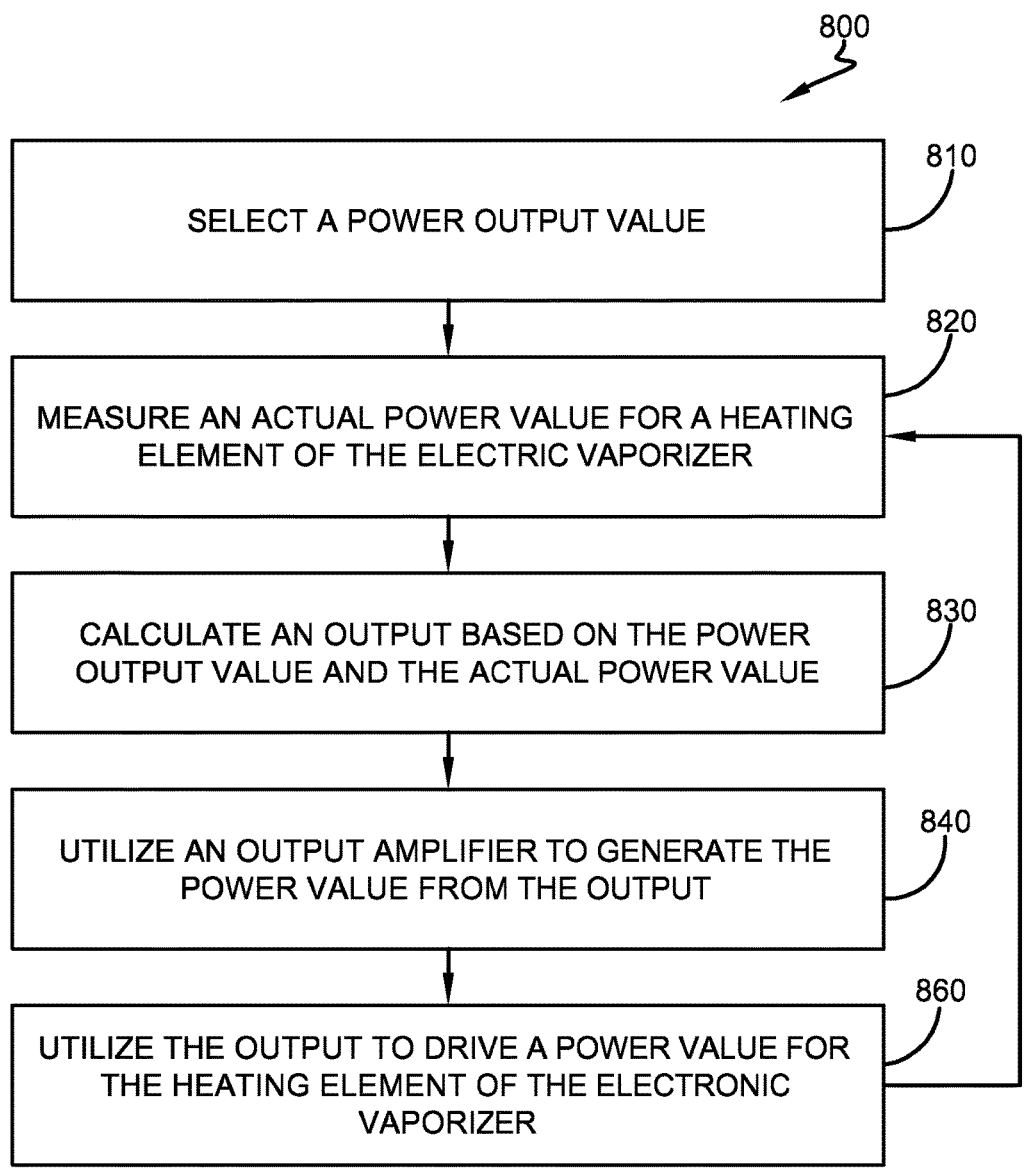
FIG. 8 illustrates a flow chart diagram of a method for controlling an electronic vaporizer based on measured power output of a heating element.

In view of the exemplary systems described supra, methodologies that may be implemented in accordance with the disclosed subject matter will be better appreciated with reference to the flow chart of FIG. 8. While for purposes of simplicity of explanation, the methodology are shown and described as a series of blocks, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methods described hereinafter.

FIG. 8 illustrates a flow chart diagram of a method 800 for controlling an electronic vaporizer based on measured power output of a heating element. At reference numeral 810, a power output value is selected. At reference numeral 820, an actual power value for a heating element of the electronic vaporizer is measured. At reference numeral 830, an output is calculated based on the power output value and the actual power value. At reference numeral 840, an output amplifier is utilized to generate the power value from the output. At reference numeral 850, the output is utilized to drive a power value for the heating element of the electronic vaporizer. After reference numeral 850, the method 800 can continue to reference numeral 820 to measure actual power for the heating element. The method can further include displaying at least one of a selected power output, a resistance of the heating element in real time, or the measured power output to the heating element in real time.

One embodiment provides an electronic vaporizer device used to simulate smoking. The device includes a power source configured to generate a power level to be delivered to a heating element for vaporizing a material during a simulated smoking session. The device also includes a power manager operatively connected to the power source and configured to regulate the power level delivered to the heating element to a wattage setting during activation of the electronic vaporizer device, to consistently control a quantity and a quality of vapor produced by the electronic vaporizer device. The device may also include a trigger component operatively connected to the power manager and configured to activate the electronic vaporizer device via the power manager. The trigger component may include at least one of an input from a user, a button input, a voice command, a touch screen input, a motion detection, a pressure switch, a pressure sensor, a flow sensor, or a proximity sensor input. The power manager may be configured to provide an input signal to the power source to adjust at least one of a current or a voltage provided by the power source to regulate the power level delivered to the heating element to the wattage setting during activation of the electronic vaporizer device. The power manager may be configured to adjust at least one of a current or a voltage output by the power source to regulate the power level delivered to the heating element to the wattage setting during activation of the electronic vaporizer device. The power manager may be configured to sense at least one of a current or a voltage applied to the heating element in real time. The power manager may be configured to determine a resistance of the heating element in real time. The power manager may be configured to simultaneously measure or sense at least two of a resistance of the heating element, an output voltage of the heating element, and an output current of the heating element as part of regulating the power level delivered to the heating element.

One embodiment provides an electronic vaporizing system used to simulate smoking. The system includes a cartridge containing a heating element for vaporizing a material for inhaling, and an electronic vaporizer device operatively connected to the cartridge. The electronic vaporizer device is configured to generate a power level to be delivered to the heating element, and regulate the power level to a wattage setting during activation of the electronic vaporizer device to provide a consistent vapor during the simulated smoking session. The electronic vaporizer device may be configured to allow a user to activate the electronic vaporizer device to initiate delivery of the power level to the heating element. The cartridge may be configured to allow a user to inhale a vaporized material produced inside the cartridge. The electronic vaporizer device may be configured as a portable electronic hand-held device. The cartridge may be configured to be connected to and disconnected from the electronic vaporizer device. The electronic vaporizer device may be configured to connect to and operate with cartridges having heating elements of different resistances. The electronic vaporizer device may be configured to regulate, in real time, the power level delivered to the heating element to the wattage setting during activation of the electronic vaporizer device, even as the resistance of the heating element changes.

One embodiment provides a method to simulate smoking with an electronic vaporizer device and a cartridge. The method includes regulating a power level delivered to a heating element of a cartridge connected to an electronic vaporizer device, for vaporizing a material within the cartridge during a simulated smoking session, to a wattage setting during activation of the electronic vaporizer device to provide a consistent quantity and quality of vapor during the simulated smoking session. The regulating of the power level, delivered to the heating element, to the wattage setting may be performed in real time regardless of a resistance of the heating element of the cartridge. The regulating of the power level, delivered to the heating element, to the wattage setting may be performed in real time regardless of a change in a resistance of the heating element of the cartridge during the simulated smoking session.

One embodiment provides a controller. The controller includes a circuit configured to be operatively connected to at least a user input device, a power supply, and a heating element. The controller is further configured to regulate a power level delivered to the heating element from the power supply substantially to a user-selected wattage setting, regardless of heating element parameters and a state of the power supply, to consistently control a quantity and a quality of vapor produced when a liquid material is heated by the heating element.

One embodiment provides an electronic vaporizer device used to simulate smoking. The device includes a power source configured to generate a power level being a determined wattage level to be delivered to a heating element for vaporizing a material during a simulated smoking session. The device also includes a power manager operatively connected to the power source and configured to regulate the power level delivered to the heating element to substantially the determined wattage level during activation of the electronic vaporizer device, to consistently control a quantity and a quality of vapor produced by the electronic vaporizer device.

What has been described above includes examples of the subject innovation. It is, of course, not possible to describe every conceivable combination of components or methodologies for purposes of describing the claimed subject matter, but one of ordinary skill in the art may recognize that many further combinations and permutations of the subject innovation are possible. Accordingly, the claimed subject matter is intended to embrace all such alterations, modifications, and variations that fall within the spirit and scope of the appended claims.

As used herein, the terms "component" and "system," as well as forms thereof are intended to refer to a computer-related entity, either hardware, a combination of hardware and software, software, or software in execution. For example, a component may be, but is not limited to being, a process running on a processor, a processor, an object, an instance, an executable, a thread of execution, a program, and/or a computer. By way of illustration, both an application running on a computer and the computer can be a component. One or more components may reside within a process and/or thread of execution and a component may be localized on one computer and/or distributed between two or more computers.

The word "exemplary" or various forms thereof are used herein to mean serving as an example, instance, or illustration. Any aspect or design described herein as "exemplary" is not necessarily to be construed as preferred or advantageous over other aspects or designs. Furthermore, examples are provided solely for purposes of clarity and understanding and are not meant to limit or restrict the claimed subject matter or relevant portions of this disclosure in any manner. It is to be appreciated a myriad of additional or alternate examples of varying scope could have been presented, but have been omitted for purposes of brevity.

Specific embodiments of an innovation are disclosed herein. One of ordinary skill in the art will readily recognize that the innovation may have other applications in other environments. In fact, many embodiments and implementations are possible. The following claims are in no way intended to limit the scope of the subject innovation to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means".

Although the subject innovation has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (e.g., components, etc.), the terms (including a reference to a "means") used to describe such elements are intended to correspond, unless otherwise indicated, to any element which performs the specified function of the described element (e.g., that is functionally equivalent), even though not structurally equivalent to the disclosed structure which performs the function in the herein illustrated exemplary embodiment or embodiments of the innovation. In addition, while a particular feature of the innovation may have been described above with respect to only one or more of several illustrated embodiments, such feature may be combined with one or more other features of the other embodiments, as may be desired and advantageous for any given or particular application. Although certain embodiments have been shown and described, it is understood that equivalents and modifications falling within the scope of the appended claims will occur to others who are skilled in the art upon the reading and understanding of this specification.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

What is claimed is:

1. A controller, comprising:
a circuit configured to be operatively connected to at least a user input device, a power supply, and a heating element, and further configured to regulate a power level delivered to the heating element from the power supply substantially to a user-selected wattage setting input via the user input device by dynamically varying at least one of a current and a voltage supplied to the heating element during a simulated smoking session, wherein the power level is regulated substantially to the user-selected wattage regardless of heating element parameters within an operating range and a state of the power supply, to consistently control a quantity and a quality of vapor produced when a liquid material is heated by the heating element during the simulated smoking session.

2. The controller of claim 1, wherein the controller further comprises a trigger component within the circuit, the trigger component being connected between the power supply and the heating element and operable to selectively connect the power supply to the heating element.

3. The controller of claim 2, wherein the trigger component includes at least one of an input from a user, a button input, a voice command, a touchscreen input, a motion detection, a pressure switch, a pressure sensor, a flow sensor or a proximity sensor input.

4. The controller of claim 1, wherein the circuit is further configured to provide an input signal to a power source to adjust at least one of a current or a voltage provided by the power source to regulate the power level delivered to the heating element.

5. The controller of claim 1, wherein the circuit is configured to sense the at least one of the current and the voltage supplied to the heating element in real time.

6. The controller of claim 1, wherein the circuit is configured to determine a resistance of the heating element in real time.

7. The controller of claim 1, wherein the circuit further comprises a display configured to display at least one of the wattage settings, a real time watt output, a resistance of the heating element, and the at least one of the current and the voltage supplied to the heating element.

8. The controller of claim 1, wherein the circuit is configured to simultaneously measure or sense at least two of a resistance of the heating element, an output voltage of the heating element, and an output current of the heating element.

9. The controller of claim 1, wherein the circuit is configured to simultaneously control at least one of a resistance of the heating element, an output voltage of the heating element, and an output current of the heating element while measuring another of the resistance of the heating element, the output voltage of the heating element, and the output current of the heating element.

10. The controller of claim 1, wherein the circuit is configured to determine at least one of an input power of the heating element, a combination of an input voltage, an output voltage, a current, and a resistance of the heating element, and a converter efficiency to regulate the power level delivered to the heating element.

11. The controller of claim 1 wherein the circuit is configured to utilize at least one of a feedback control loop and a feed forward control loop to regulate the power level delivered to the heating element.

12. The controller of claim 11, wherein the at least one of the feedback, the feed forward, and the control loop employ a sample rate between a range of 1 Hz to 2,500 Hz.

13. The controller of claim 11, wherein the at least one of the feedback, feed forward and control loop are continuous.

14. The controller of claim 1, wherein the circuit includes a:
   a control loop;
   a voltage sense;
   a current sense; and
   a regulator, wherein the control loop receives a power input signal and a calculated power signal from the voltage sense and current sense to generate an output power signal to the regulator and, wherein the regulator communicates the output power signal to the converter.

15. The controller of claim 14, wherein the converter is a boost converter.

16. The controller of claim 14, wherein the control loop generates a pulse with modulation signal to the regulator.

17. The controller of claim 14, wherein the voltage sense and current sense calculate a measured resistance.

18. The controller of claim 14, wherein the control loop includes at least one of a proportional control, an integral control and a feed forward control.

* * * * *